(12) United States Patent
Pandey et al.

(10) Patent No.: US 7,947,729 B2
(45) Date of Patent: May 24, 2011

(54) ADDUCT OF FLUORESCENT DYE AND TUMOR AVID TETRAPYRROLE

(75) Inventors: Ravindra K. Pandey, Williamsville, NY (US); Yihui Chen, Amherst, NY (US); William Potter, E. Amherst, NY (US); Allan Oseroff, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 222 days.

(21) Appl. No.: 11/632,433

(22) PCT Filed: Jul. 13, 2005

(86) PCT No.: PCT/US2005/024782
§ 371 (c)(1),
(2), (4) Date: Aug. 7, 2008

(87) PCT Pub. No.: WO2006/019775
PCT Pub. Date: Feb. 23, 2006

(65) Prior Publication Data
US 2009/0043090 A1     Feb. 12, 2009

Related U.S. Application Data

(60) Provisional application No. 60/588,876, filed on Jul. 16, 2004.

(51) Int. Cl.
*C07B 47/00* (2006.01)
*C07D 487/22* (2006.01)
(52) U.S. Cl. .................. 514/410; 514/912; 540/145
(58) Field of Classification Search .................. 540/145; 514/185, 410, 912
See application file for complete search history.

(56) References Cited

U.S. PATENT DOCUMENTS

| | | | |
|---|---|---|---|
| 4,649,151 A | 3/1987 | Dougherty | |
| 4,866,168 A | 9/1989 | Dougherty | |
| 4,889,129 A | 12/1989 | Dougherty | |
| 4,932,934 A | 6/1990 | Dougherty | |
| 4,968,715 A | 11/1990 | Dougherty | |
| 5,002,962 A | 3/1991 | Pandey | |
| 5,015,463 A | 5/1991 | Dougherty | |
| 5,028,621 A | 7/1991 | Dougherty | |
| 5,145,863 A | 9/1992 | Dougherty | |
| 5,198,460 A | 3/1993 | Pandey | |
| 5,225,433 A | 7/1993 | Dougherty | |
| 5,314,905 A | 5/1994 | Pandey | |
| 5,459,159 A | 10/1995 | Pandey | |
| 5,498,710 A | 3/1996 | Pandey | |
| 5,591,847 A | 1/1997 | Pandey | |
| 5,707,986 A * | 1/1998 | Miller et al. ............. | 514/185 |
| 6,103,751 A | 8/2000 | Pandey | |

OTHER PUBLICATIONS

Pinedo et al., "Translational Research . . . ", The Oncologist 2000,, 5 (suppl1): 1-2 (www.The Oncologist .com).*

McMahon, Gerald, "VEGF Receptor Signaling in Tumor Angiogenesis", The Oncologist 2000; 5(suppl 1): 3-10 (www.The Oncologist.com).*
"Use of the Chlorophyll Derivative Purpurin-18, for Synthesis of Sensitizers for Use in Photodynamic Therapy", Lee et al., J.Chem. Soc., 1993, (19) 2369-77.
"New Synthesis of Benzoporphyrin Derivatives and Analogues for Use in Photodynamic Therapy", Meunier et al., Bioorganic & Midicinal Chemistry Letters, vol. 2, No. 12, pp. 1575-1580, 1992.
"Photosensitizing Properties of Bacteriochlorophyllin a and Bacteriochlorin a, Two Derivatives of Bacteriochlorophyll a", Beems et al., Photochemistry and Photobiology, 1987, v. 46, 639-643.
"Photoradiation Therapy. II. Cure of Animal Tumors With Hematoporphyrin and Light", Dougherty et al., Journal of the National Cancer Institute, Jul. 1975, v. 55, 115-119.
"Photodynamic therapy of C3H mouse mammary carcinoma with hematoporphyrin di-esters as sensitizers", Evensen et al., Br. J. Cancer, 1987, 55, 483-486.
"Substituent Effects in Tetrapyrrole Subunit Reactivity and Pinacol-Pinacolone Rearrangements: VIC-Dihydroxychlorins and VIC-Dihydroxybacteriochlorins" Pandey et al., Tetrahedron Letters, 1992, v. 33, 7815-7818.
"Photodynamic Sensitizers from Chlorophyll: Purpurin-18 and Chlorin p6", Hoober et al., 1988, v.48, 579-582.
"Structure/Activity Relationships Among Photosensitizers Related to Pheophorbides and Bacteriopheophorbides", Pandey et al., Bioorganic and Medicinal Chemistry Letters, 1992, v 2, 491-496.
"Chemistry of Photofrin II and Some New Photosensitizers", Pandey et al., Photodynamic Therapy: Mechanisms (1989) (SPIE), vol. 1065, pp. 164-174.
"Fast Atom Bombardment Mass Spectral Analyses of Photofrin II and its Synthetic Analogs", Pandey et al., Biomedical and Environmental Mass Spectrometry, 1990, v. 19, 405-414.
"Indocyanine Green as A Prospective Sensitizer for Photodynamic Therapy of Melanomas", Krystyna et al., Acta Biochimica Polonica, 2002, v. 49, No. 2/2002, 387-391 Quarterly.
"Hydrophilic Cyanine Dyes as Contrast Agents for Near-Infrared Tumor Imaging; Synthesis, Photophysical Properties and Spectroscopic in vivo Characterization", Licha et al., BioOne, 2000, vol. 72, Issue 3, pp. 392-398.
"Ultraviolet Spectrum/Light The Cause of Color"; 7th Grade Science, Chasteen T.G., Sam Houston State University, Dept. of Chemistry; Jun. 12, 2003 from www.shsu.edu/%7Echm_tcg/sounds/sound.html (instrumentation video clips).

* cited by examiner

*Primary Examiner* — Paul V. Ward
(74) *Attorney, Agent, or Firm* — Michael L. Dunn

(57) ABSTRACT

A compound having preferential localization in tumor tissue relative to normal tissue, a preferential electromagnetic absorption at a wavelength between about 660 and 900 nm, and a fluorescence at a wavelength shifted from the preferential absorption by at least +30 nm and preferably at least +50 nm. The compound further preferably destroys tumor tissue in which it is absorbed when exposed to light at its preferential absorption wavelength. In a preferred embodiment of the invention, the compound is a conjugate of a tumor avid tetrapyrrole compound with a fluorescent dye, and more preferably the fluorescent dye is an indocyanine dye such as indocyanine green. The tumor avid tetrapyrrole compound is preferably a porphyrin derivative selected from the group consisting of chlorins, bacteriochlorins, purpurins and derivatives thereof.

7 Claims, 9 Drawing Sheets

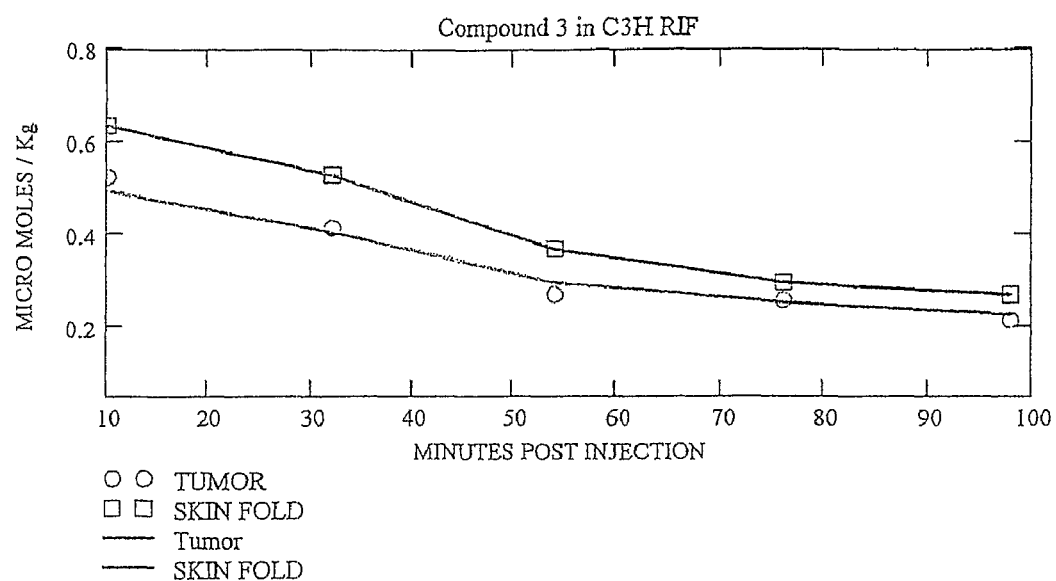
Figure 5: Tumor (red) versus skin uptake of compound 1 (ICG, 5.0 μmole/kg) alone at 24 h post-injection

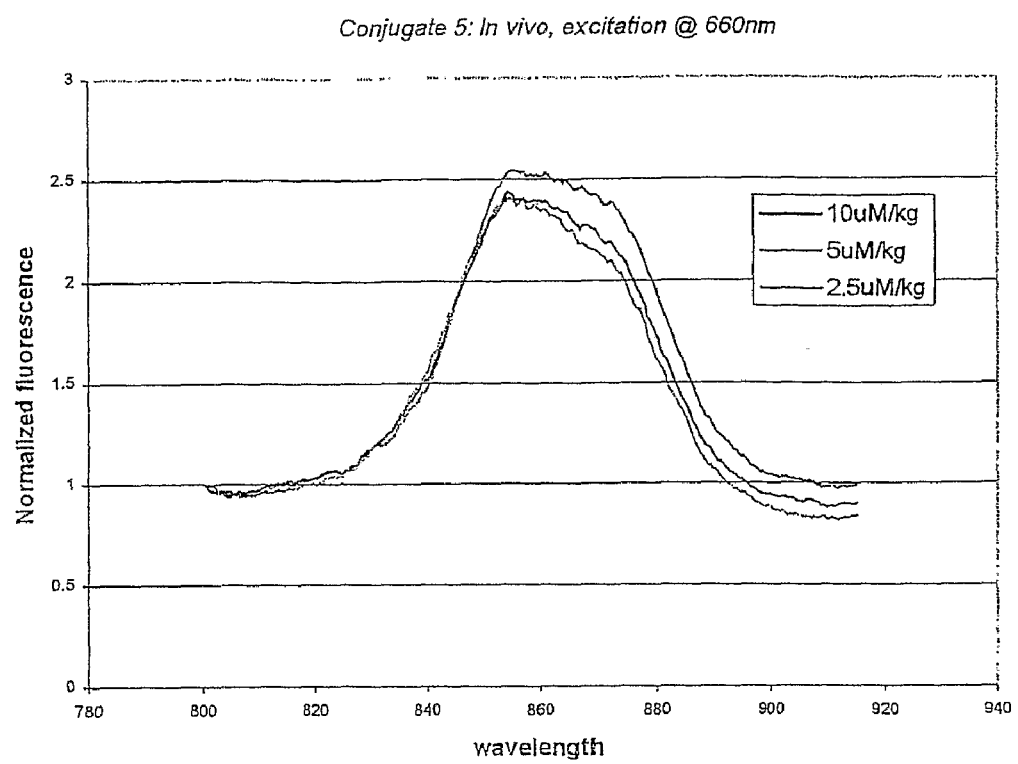
Figure 6: *In vivo* (tumor) fluorescence spectra of conjugate 4 in mice at variable drug doses

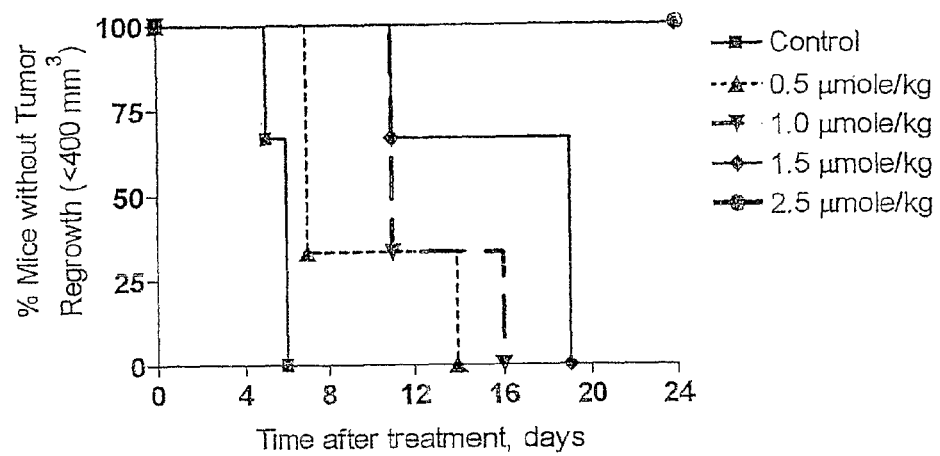
Figure 7: *In vivo* photosensitizing of conjugate 5 in C3H mice bearing RIF tumors at variable doses. The tumors were exposed to a laser light at 660 nm (135 J/cm$^2$) at 24 h post injection.

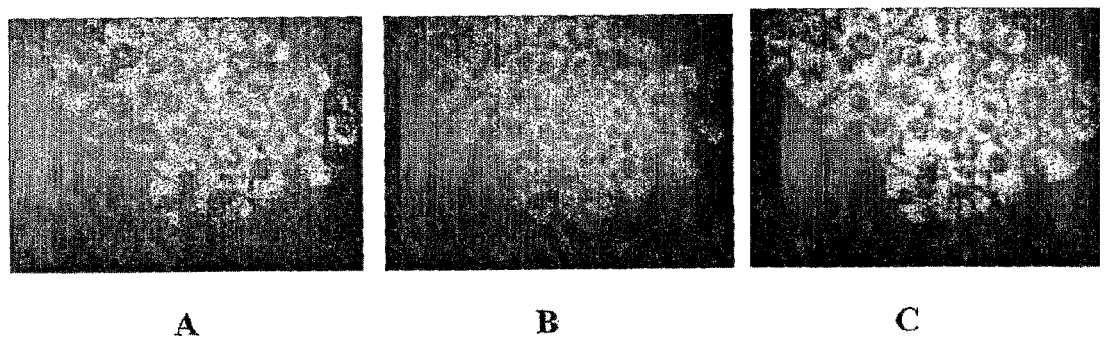
Figure 8: Comparative intracellular localization of bacteriopurpurinimde 5 with Mito Tracker® Green.
A: Compound 5; B: Mito Tracker® Green; C: Overlay (A and B)

Figure 9: *In vivo* photosensitizing efficacy of the conjugate in C3H mice (10 mice/group) transplanted with RIF tumors at variable doses. The tumors were exposed to light (135 J/cm$^2$) for 30 min at 24 h post injection
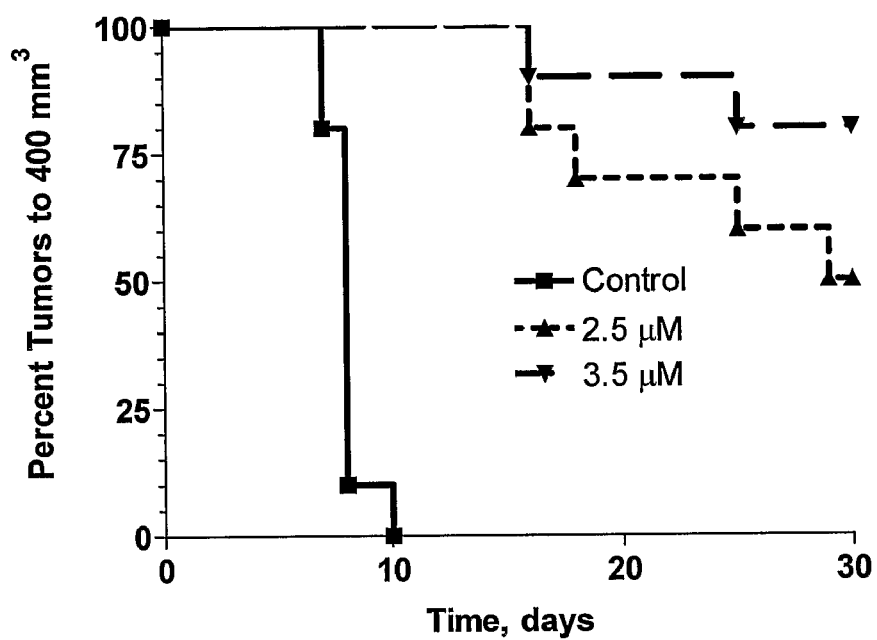

ADDUCT OF FLUORESCENT DYE AND TUMOR AVID TETRAPYRROLE

CROSS REFERENCE TO RELATED APPLICATIONS

This is a United States Nationalization of International Patent Application PCT/US05/24782 filed Jul. 13, 2005 which claims priority from U.S. Provisional Application 60/588,876 filed Jul. 16, 2004.

STATEMENT REGARDING FEDERALLY SPONSORED RESEARCH

This invention was made with government support under Grant Numbers CA127369 and CA055791 awarded by the National Institute of Health. The government has certain rights in this invention.

BACKGROUND OF THE INVENTION

The detection of early neoplastic changes is important from an outcome point of view because once invasive carcinoma and metastasis have occurred, treatment is difficult. At present, excisional biopsy followed by histology is considered the "gold standard" for diagnosis of early neoplastic changes and carcinoma. In some cases, cytology, i.e. analysis by surface or excretory cells, rather than excisional biopsy, is performed. These techniques are powerful diagnostic tools because they provide high-resolution spatial and morphological information of the cellular and subcellular structure of tissues. The use of staining and processing can enhance contrast and specificity of histopathology. However, both of these diagnostic procedures require physical removal of specimens followed by tissue processing in the laboratory. These procedures incur a relatively high cost because specimen handling is required and more importantly diagnostic information is not immediately available.

Fluorescence techniques have the potential for performing in vivo diagnosis on tissue without the need for sampling excision and processing and in recent years, the use of fluorescence spectroscopy has been explored for diagnosis of cancer. Infrared imaging (IRI) using a spectroscopic agent, has several advantages over in vitro and other in vivo techniques in that the technique is non-invasive and under proper conditions can give deep penetration and quantitative results and a more complete examination of an organ of interest can be achieved than with excisional biopsy or cytology. Further, in testing fluorescent materials, the complete profile of uptake, retention and elimination of needed spectroscopic agents can be followed within a single laboratory animal thus reducing the number of animals required in preclinical trials.

The requirements for an ideal spectroscopic agent needed for infrared imaging techniques are as follows: i) it should preferentially localize in tumor cells; ii) it should have high fluorescent efficiency; iii) it should not produce phototoxicity or other adverse effects in a patient; iv) it should be easy to synthesize; v) it should be chemically pure; and vi) it should have a long wave length emission so that deep seated tumors can be detected.

Porphyrins including chlorins, bacteriochlorins and other porphyrin based derivatives, including their analogs and derivatives, have recently found superior utility as photodynamic compounds for use in diagnosis and treatment of disease, especially certain cancers and other hyperproliferative diseases such as macular degeneration. These compounds have also found utility in treatment of psoriasis and papillomatosis.

Such derivatives include dimers and trimers of these compounds. Permissible derivatives also include ring variations of these compounds; provided that, the central sixteen sided four nitrogen heterocycle of these compounds remains intact. Chlorophyllins, purpurins and pheophorbides and their derivatives are, therefore, included within "porphyrins, chlorins, and bacteriochlorins and their derivatives and analogs". Such derivatives include modifications of substituents upon these ring structures.

Numerous articles have been written on this subject, e.g. "Use of the Chlorophyll Derivative Purpurin-18, for Synthesis of Sensitizers for Use in Photodynamic Therapy", Lee et al., J. Chem. Soc., 1993, (19) 2369-77; "Synthesis of New Bacteriochlorins And Their Antitumor Activity", Pandey et al., Biology and Med. Chem. Letters, 1992; "Photosensitizing Properties of Bacteriochlorophyllin a and Bacteriochlorin a, Two Derivatives of Bacteriochlorophyll a", Beems et al., Photochemistry and Photobiology, 1987, v. 46, 639-643; "Photoradiation Therapy. II. Cure of Animal Tumors With Hematoporphyrin and Light", Dougherty et al., Journal of the National Cancer Institute, July 1975, v. 55, 115-119; "Photodynamic therapy of C3H mouse mammary carcinoma with hematoporphyrin di-esters as sensitizers", Evensen et al., Br. J. Cancer, 1987, 55, 483-486; "Substituent Effects in Tetrapyrrole Subunit Reactivity and Pinacol-Pinacolone Rearrangements: VIC-Dihydroxychlorins and VIC-Dihydroxybacteriochlorins" Pandey et al., Tetrahedron Letters, 1992, v. 33, 7815-7818; "Photodynamic Sensitizers from Chlorophyll: Purpurin-18 and Chlorin $p_6$", Hoober et al., 1988, v.48, 579-582; "Structure/Activity Relationships Among Photosensitizers Related to Pheophorbides and Bacteriopheophorbides", Pandey et al., Bioorganic and Medicinal Chemistry Letters, 1992, v 2, 491-496; "Photodynamic Therapy Mechanisms", Pandey et al., Proceedings Society of Photo-Optical Instrumentation Engineers (SPIE), 1989, v 1065, 164-174; and "Fast Atom Bombardment Mass Spectral Analyses of Photofrin II® and its Synthetic Analogs", Pandey et al., Biomedical and Environmental Mass Spectrometry, 1990, v. 19, 405-414. These articles are incorporated by reference herein as background art.

Numerous patents in this area have been applied for and granted world wide on these photodynamic compounds. Reference may be had, for example to the following U.S. Pat. Nos. which are incorporated herein by reference: 4,649,151; 4,866,168; 4,889,129; 4,932,934; 4,968,715; 5,002,962; 5,015,463; 5,028,621; 5,145,863; 5,198,460; 5,225,433; 5,314,905; 5,459,159; 5,498,710; and 5,591,847.

One of these compounds "Photofrin®" has received approval for use in the United States, Canada and Japan. Others of these compounds have also received at least restricted approval, e.g. BPD for treatment of macular degeneration and others are in clinical trials or are being considered for such trials.

The term "porphyrins, chlorins and bacteriochlorins" as used herein is intended to include their derivatives and analogs, as described above, and as described and illustrated by the foregoing articles and patents incorporated herein by reference as background art.

Such compounds have been found to have the remarkable characteristic of preferentially accumulating in tumors rather than most normal cells and organs, excepting the liver and spleen. Furthermore, many such tumors can be killed because the compounds may be activated by light to become tumor toxic.

Such compounds are preferentially absorbed into cancer cells, and destroy cancer cells upon being exposed to light at their preferential wavelength absorbance near infrared (NIR) absorption. Further such compounds emit radiation at longer wavelengths than the preferential absorption wavelength, such that light penetrates several centimeters of tissue. It is thus possible to sense and quantitate photosensitizer concentration in subsurface tissues from measurements of diffuse light propagation. It has thus been proposed that diffuse NIR light might be used to detect and image diseased subsurface tissues based upon special variations in NIR absorbance, fluorescence, and fluorescence decay kinetics associated with PDT drugs and other fluorescent agents. It has been shown that the frequency-domain photon migration (FDPM) with image-intensified charge coupled device (CCD) can be used for the detection of in vivo diseased tissues using fluorescent contrast agents. Porphyrin-based compounds, as above described, are highly fluorescent thus this characteristic has been explored for investigating their utility as optical imaging agents. Unfortunately, these compounds do not generally show a sufficient shift ("Stoke's Shift") between absorption and emission to be suitable for this purpose and thus such compounds do not provide a good means for detection, i.e. fluorescent emission wavelengths of such compounds are close to the wavelengths of their preferential absorbance thus causing detection interference.

One approach has been to modify a porphyrin structure to permit emission at a longer wavelength, e.g. as described in U.S. Pat. No. 6,103,751 for "Carotene Analogs of Porphyrins, Chlorins and Bacteriochlorins as therapeutic and Diagnostic Agents". Unfortunately, the effect of adding the carotene moiety to the porphyrin so reduced therapeutic effects that its use for therapeutic treatment is impractical thus making it clear that such structures could not be modified without an expectation of loss of valuable properties in exchange for improvement of emission wavelength.

A number of compounds that fluoresce at detectable wavelengths are, however, known that have been investigated and used for the diagnosis of almost every type of cancer, in particular early neoplastic changes found in humans. There nevertheless have been significant difficulties with such an approach due to several factors including lack of significant preferential tumor absorbance, toxicity, and lack of sufficient penetration both for activation of fluorescing compounds and for emissions that have sufficient penetration to be detected outside of the tumor or organism. Further, such compounds, while possibly having detecting potential, do not function to destroy tumors and other hyperprolific tissues.

It would therefore be desirable to have a physiologically compatible compound:
1. having preferential localization in tumor tissue relative to normal tissue,
2. having high fluorescent efficiency,
3. that should not be toxic, phototoxic, carcinogenic or teratologic,
4. that should be easy to synthesize,
5. that should be chemically pure,
6. that should have a long wavelength absorption in the range of 600 to 800 nm so that deep seated tumors can be detected,
7. that should destroy tumors in which it is localized by activation, and
8. that should have an emission wavelength sufficiently separated (shifted) from its preferential absorption wavelength so as to prevent significant interference so that tumors can be easily detected by in vivo fluorescence spectroscopy.

BRIEF DESCRIPTION OF THE INVENTION

The invention comprises a compound having preferential localization in tumor tissue relative to normal tissue, a preferential electromagnetic absorption at a wavelength between about 660 and 900 nm, and a fluorescence at a wavelength shifted from the preferential absorption by at least +30 nm and preferably at least +50 nm. The compound further preferably destroys tumor tissue in which it is absorbed when exposed to light at its preferential absorption wavelength. In a preferred embodiment of the invention, the compound is a conjugate of a tumor avid tetrapyrrole compound with a fluorescent dye, and more preferably the fluorescent dye is an indocyanine dye such as indocyanine green. The tumor avid tetrapyrrole compound is preferably a porphyrin derivative selected from the group consisting of chlorins, bacteriochlorins, purpurins and derivatives thereof (collectively "porphyrins") and usually has the generic formula:

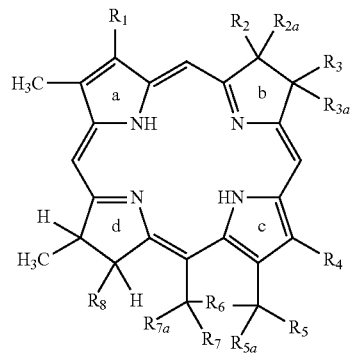

where:
$R_1$ is, substituted or unsubstituted, —CH=CH$_2$, —CHO, COOH, or

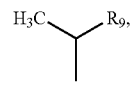

where $R_9$=—OR$_{10}$ where $R_{10}$ is lower alkyl of 1 through 8 carbon atoms, or —(CH$_2$—O)$_n$CH$_3$; $R_2$, $R_{2a}$, $R_3$, $R_{3a}$, $R_4$, $R_5$, $R_{5a}$, $R_7$, and $R_{7a}$ are independently hydrogen, lower alkyl, substituted lower alkyl, lower alkylene or substituted lower alkylene or two $R_2$, $R_{2a}$, $R_3$, $R_{3a}$, $R_5$, $R_{5a}$, $R_7$, and $R_{7a}$ groups on adjacent carbon atoms may be taken together to form a covalent bond or two $R_2$, $R_{2a}$, $R_3$, $R_{3a}$, $R_5$, $R_{5a}$, $R_7$, and $R_{7a}$ groups on the same carbon atom may form a double bond to a divalent pendant group; $R_2$ and $R_3$ may together form a 5 or 6 membered heterocyclic ring containing oxygen, nitrogen or sulfur; $R_6$ is —CH$_2$—, —NR$_{11}$—, where $R_{11}$ is, substituted or unsubstituted, lower alkyl, or lower alkylene; or a $R_6$ is a covalent bond; $R_8$ is —(CH$_2$)$_2$CO$_2$R$_{12}$ where $R_{12}$ is, substituted or unsubstituted, lower alkyl, lower alkylene or —NH$_2$.

Usually at least one of $R_1$, $R_{2a}$, $R_3$, $R_{3a}$, $R_4$, $R_5$, $R_{5a}$, $R_7$, $R_{7a}$, $R_8$, $R_9$, $R_{10}$, $R_{11}$, or $R_{12}$ is substituted with a dye fluorescing at a wave length of from about 800 to about 900 nm.

The fluorescent dye may be any non-toxic dye that causes the conjugate to preferentially emit (fluoresce) at a wave length of 800 to about 900 nm. Such dyes usually have at least two resonant ring structures, often chromophores, connected together by an intermediate resonant structure of conjugated double bonds, aromatic carbon rings, resonant heterocyclic rings, or combinations thereof.

Examples of such dyes include bis indole dyes wherein two indole or modified indole ring structures are connected together at their 3$^2$ and 2$^1$ carbon atoms respectively by an intermediate resonant structure as previously described. Such dyes are commonly known as tricarbocyanine dyes. Such dyes almost always have at least one, and usually at least two, hydrophilic substituents making the dye water soluble. Such water solubility facilitates entry of the structure into an organism and its cellular structures and reduces the likelihood of toxicity because of reduced storage in fatty tissues and fast elimination from the system. The intermediate resonant structure usually contains a plurality of double bonded carbon atoms that are usually conjugated double bonds and may also contain unsaturated carbocyclic or heterocyclic rings. Such rings permit conjugation to the porphyrin structure without significantly interfering with the resonance of the intermediate structure.

The invention further includes a method for using the compound of the invention for detection of tumors by injection into an organism, allowing sufficient time for preferential absorption into tumor tissue, exposing the absorbed compound to light at its preferential absorption wavelength and detecting the location of emissions from the preferentially absorbed compound to locate tumor tissue and includes a method for treating tumor tissue by injection into an organism, allowing sufficient time for preferential absorption into tumor tissue, and exposing the absorbed compound to light at its preferential absorption wavelength to cause destruction of tumor tissue. It is to be understood that the destruction of tumor tissue in accordance with the invention may be accomplished at a part of the method for detection.

BRIEF DESCRIPTION OF THE DRAWINGS

The nature and mode of operation of the present invention will now be more fully described in the following detailed description of the invention taken with the accompanying drawing figures, in which:

FIG. 5 shows tumor uptake of conjugate 5 relative to indocuzanine ? analog alone;

FIG. 6 shows vivo fluorescence of conjugate 5 at various injective concentrations 24 hours post injection;

FIG. 7 shows effectiveness of tumor treatment by photodynamic therapy using conjugate 5 at various concentrations;

FIG. 8 shows photosensitizer localization of conjugate 5 in mitochondria relative to a known mitochondrial probe; and FIG. 9 shows in vivo effectiveness of conjugate 5 transplanted with RIF tumors at variable doses 24 hours post injection.

DETAILED DESCRIPTION OF THE INVENTION

Figure 1:
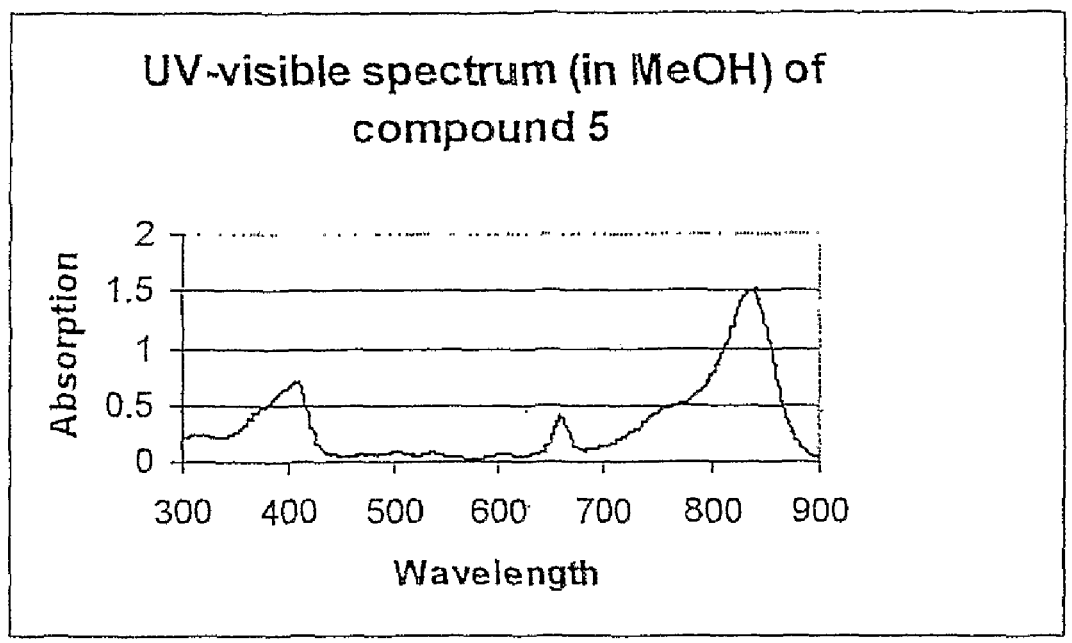
FIG. 1 is a graph of the UV-visible spectrum of conjugate 5.

"Preferential electromagnetic absorption at a wavelength between about 660 and 900 nm" means that within a UV band of from about 300 to 900 nm there is a peak absorbance between 660 and 900 nm that is at least twice and usually at least three times that of any other peak absorbance within the band. "A fluorescence at a wavelength shifted from the preferential absorption by at least +30 nm and preferably at least +50 nm" means that emission (fluorescence) wavelength, resulting from excitation at the preferential absorption wavelength, is shifted upwardly from the peak absorbance wavelength by at least 30 and preferably at least 50 nm. While not essential in accordance with the invention, the compound further preferably destroys tumor tissue in which it is absorbed when exposed to light at its preferential absorption wavelength. It is believed that this occurs due to the localized formation of singlet oxygen within cancer tissue in which the compound is preferentially absorbed.

As previously discussed, in a preferred embodiment of the invention, the compound is a conjugate of a tumor avid tetrapyrrole compound with a fluorescent dye the fluorescent dye. Such dyes especially include diindole, tricarbocyanine type dyes such as indocyanine dyes that have a preferred absorbance in or about the UV wavelength range of from about 300 to 900 nm and an emission at from about 600 to about 900 nm. An example of such a dye is indocyanine green. A generic structure for other suitable diindole type dyes is as follows:

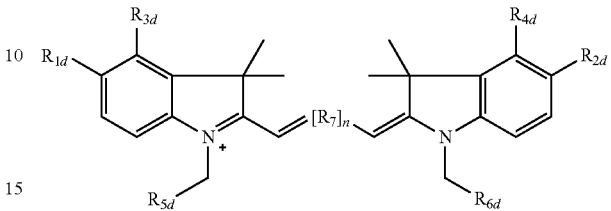

where $R_{1d}$, $R_{2d}$, $R_{3d}$, and $R_{4d}$ are hydrogen, sulfonyl, amino, carboxy, hydroxy or alkyl; provided that, $R_{1d}$ and $R_{3d}$, and $R_{2d}$ and $R_{4d}$ can be taken together to form a cycloalkenyl, aromatic or heterocyclic ring structure; $R_{5d}$ and $R_{6d}$ are independently hydrogen, alkyl, or substituted alkyl where the substituent is carboxy, sulfonyl, hydroxyl, amido, amino, alkyl ester, or halo or acid salts thereof; and $R_{7d}$ is a conjugated double bonded carbon chain, or a resonant ring selected from the group consisting of aryl, unsaturated cycloalkyl, and resonant unsaturated heterocyclic rings, which resonant ring may be substituted with a halo, amino, or carboxy group and n is an integer of 0 through 3. In a preferred dye of the above structure $R_{7d}$ is

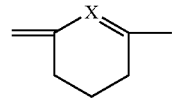

where X is halogen.

Specific examples of types of dyes for use in accordance with the invention are as follows: indocyanine green (a diindole, i.e. tricarbocyanine, dye); indocyanine green 820 nm analog CAS172616-80-7 ($R_{7d}$ is

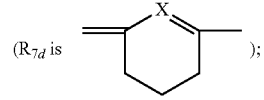

fast green FCF (FD&C green 3, a triphenylmethane dye); sulphan blue (a triphenylmethane dye) and methylene blue (a thiazine dye).

The tumor avid tetrapyrrole compound is preferably a porphyrin derivative (including porphyrin related compounds whether or not actually derived from porphyrin) that is usually selected from the group consisting of chlorins, bacteriochlorins and bacteriopurpurins. The preferred porphyrin derivatives usually have the generic formula:

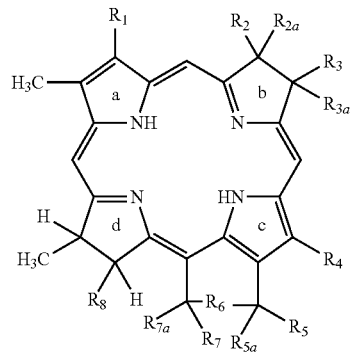

where:

$R_1$ is, substituted or unsubstituted, —CH=CH$_2$, —CHO, COOH, or

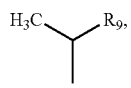

where $R_9$=—OR$_{10}$ where $R_{10}$ is lower alkyl of 1 through 8 carbon atoms, or —(CH$_2$—O)$_n$CH$_3$; $R_2$, $R_{2a}$, $R_3$, $R_{3a}$, $R_4$, $R_5$, $R_{5a}$, $R_7$, and $R_{7a}$ are independently hydrogen, lower alkyl, substituted lower alkyl, lower alkylene or substituted lower alkylene or two $R_2$, $R_{2a}$, $R_3$, $R_{3a}$, $R_5$, $R_{5a}$, $R_7$, and $R_{7a}$ groups on adjacent carbon atoms may be taken together to form a covalent bond or two $R_2$, $R_{2a}$, $R_3$, $R_{3a}$, $R_5$, $R_{5a}$, $R_7$, and $R_{7a}$ groups on the same carbon atom may form a double bond to a divalent pendant group; $R_2$ and $R_3$ may together form a 5 or 6 membered heterocyclic ring containing oxygen, nitrogen or sulfur; $R_6$ is (—CH$_2$—), —NR$_{11}$—, where $R_{11}$ is, substituted or unsubstituted, lower alkyl, or lower alkylene; or a $R_6$ is a covalent bond; $R_8$ is —(CH$_2$)$_2$CO$_2$R$_{12}$ where $R_{12}$ is, hydrogen or substituted or unsubstituted, lower alkyl, lower alkylene, an alkali or alkaline earth metal ion, or a dye moiety having a preferred absorbance in or about the UV wavelength range of from about 300 to 900 nm and an emission at from about 600 to about 900 nm., or $R_8$ is —(CH$_2$)$_2$COR$_{12a}$ where $R_{12a}$ is —NR$_2$R$_{2a}$ where $R_2$ and $R_{2a}$ are as previously described and may also contain a dye moiety having a preferred absorbance in or about the UV wavelength range of from about 300 to 900 nm and an emission at from about 600 to about 900 nm.

Usually at least one of $R_1$, $R_{2a}$, $R_3$, $R_{3a}$, $R_4$, $R_5$, $R_{5a}$, $R_7$, $R_{7a}$, $R_8$, $R_9$, $R_{10}$, $R_{11}$, or $R_{12}$ is substituted with a dye moiety fluorescing at a wavelength of from about 800 to about 900 nm. Such substitution commonly occurs at $R_8$ when $R_{12}$ is hydrogen, —NH$_2$, or —NHR$_{13}$ where $R_{13}$ is lower alkyl of 1 to 6 carbon atoms.

The invention further includes a method for using the compound of the invention for detection of tumors by injection into an organism, allowing sufficient time for preferential absorption into tumor tissue, exposing the absorbed compound to light at its preferential absorption wavelength and detecting the location of emissions from the preferentially absorbed compound to locate tumor tissue and includes a method for treating tumor tissue by injection into an organism, allowing sufficient time for preferential absorption into tumor tissue, and exposing the absorbed compound to light at its preferential absorption wavelength to cause destruction of tumor tissue. It is to be understood that the destruction of tumor tissue in accordance with the invention may be accomplished as an adjunct of the method for detection.

The compounds of the invention can be readily made from essentially any of the porphyrins including the purpurins, chlorins and bacteriochlorins discussed above in background art; provided that, such compound has a free carboxylic acid group or a free carboxylic acid ester group or a free carboxylic acid salt group, (collectively "carboxy functionality") suitable for conjugation with an appropriate dye structure as above described. Most of the porphyrins discussed in the background of the invention have such a group. In turn, the dye desirably has or is modified to have a reactive amine site that is not critical to fluorescing properties such that the dye may react at the free amine with the carboxy functionality to form the porphyrin conjugate of the invention. Such dyes may also or optionally have a reactive acid site, e.g. in the form of a sulfonic acid or carboxylic acid moiety that can react with a basic substituent on the porphyrin structure.

A generic formula for many conjugates of the invention is:

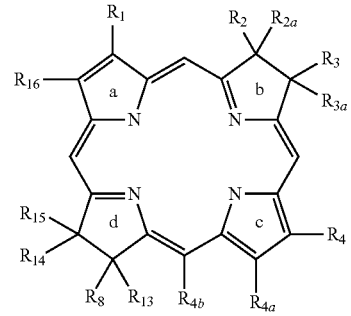

where $R_{13}$ is hydrogen or methyl; $R_8$ is —COR$_{17}$ where $R_{17}$ is —OH, —OR$_n$—NHR$_n$, where $R_n$ is lower alkyl of 1 to 8 carbon atoms, or $R_{17}$ is a dye moiety as previously described; $R_{14}$, $R_{15}$ and $R_{16}$ are independently, hydrogen, methyl or ethyl; $R_1$ and $R_2$ are independently —R$_9$, —OR$_9$, —C(R$_{12}$)(O), —C(R$_{12}$)$_2$OR$_9$, —CH=CHR$_9$, or —(CH$_2$)R$_{10}$; $R_3$ is —R$_9$, —OR$_9$, —C(R$_{12}$)(O), —C(R$_{12}$)$_2$OR$_9$, —CH=CHR$_9$, or —(CH$_2$)R$_{10}$ or taken with $R_3$ is =O; $R_{2a}$ is —R$_9$, —OR$_9$, —C(R$_{12}$)(O), —C(R$_{12}$)$_2$OR$_9$, —CH=CHR$_9$, or —(CH$_2$)R$_{14}$ or taken with $R_{3a}$ is a chemical bond; $R_{3a}$ is —R$_9$, —OR$_9$, —C(R$_{12}$)(O), —C(R$_{12}$)$_2$OR$_9$, —CH=CHR$_9$, or —(CH$_2$)R$_{10}$ or taken together with $R_{2a}$ is a chemical bond or taken with $R_3$ is =O; $R_4$ is $R_9$, or —OR$_9$; $R_9$ is, independently at each occurrence, hydrogen or lower alkyl of from 1 through about 10 carbon atoms or a dye moiety as previously described; $R_{10}$ is an amino acid residue; $R_{11}$ is —R$_9$, —R$_{10}$, or —C(O)NHR$_9$; $R_{4a}$ and $R_{4b}$ can be, independently at each occurrence, hydrogen or lower alkyl of 1 to about 4 carbon atoms or together may be —C(R$_9$)$_2$C(Y)—, —C(O)O(O)C—, —C(NR$_9$)O(O)C—, or —C(O)N(R$_{11}$)—C(O)— and Y is =O, =S, or 2H—; provided that the compound contains at least one dye moiety as previously described.

Preferred compounds of the invention may be represented by the following formula:

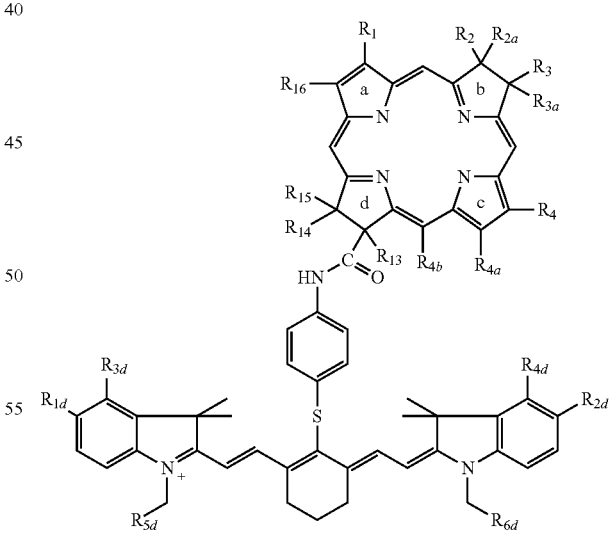

where the substituents are as previously described.

An example of a schematic diagram showing preparation of a preferred compound using HPPH and indocyanine green 820 nm analog (1), as previously described, in accordance with the present invention, where the substituents on carbon atoms a-d, f-g and m-o are usually hydrogen but may be lower alkyl, is as follows:

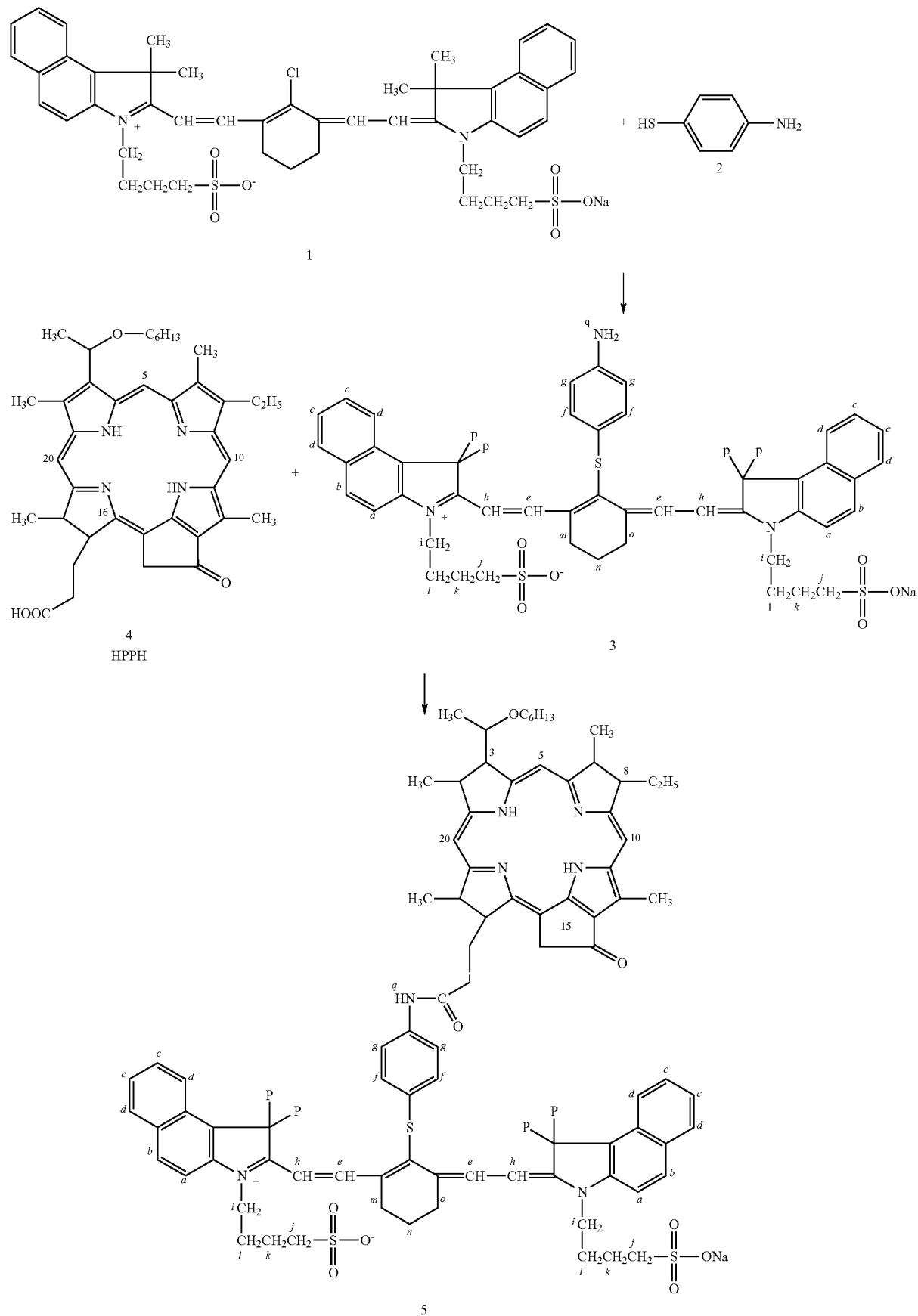

A specific preferred compound of the invention is:

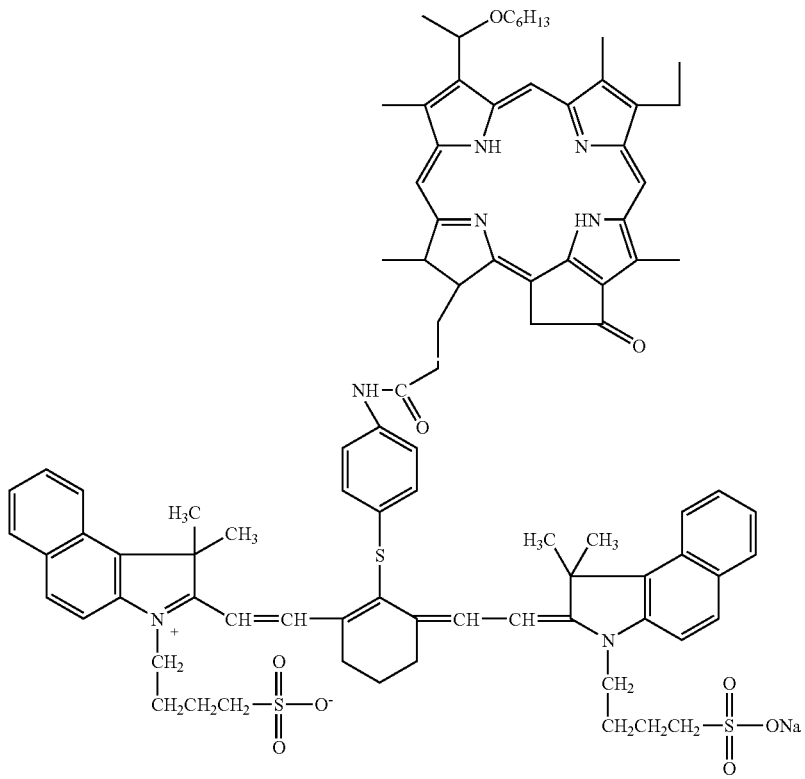

Generically many preferred compounds of the invention may be simply represented as follows:

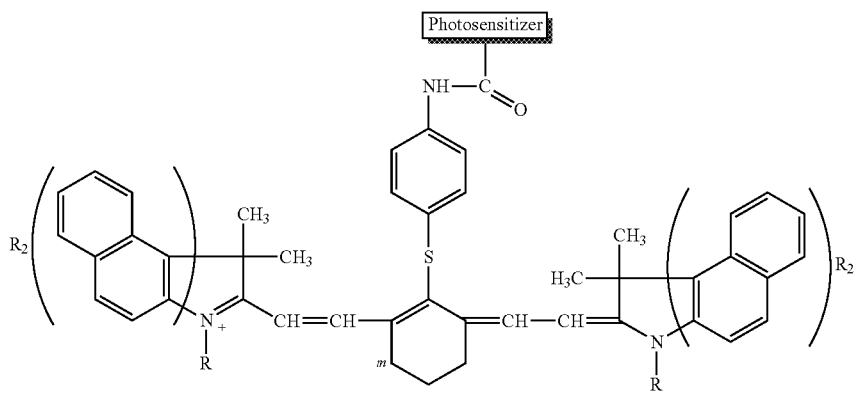

Photosensitizer: Porphyrins, Chlorins, Bacteriochlorins, Phthalocyanines, Expanded Porphyrins.
R=Alkyl, Sulfonic acid or carboxylic groups containing carbon chains with variable carbon units.
$R_2$=Various aromatic systems with and without fluorinated substituents Other preferred photosensitizer compounds of the invention may be represented as follows:

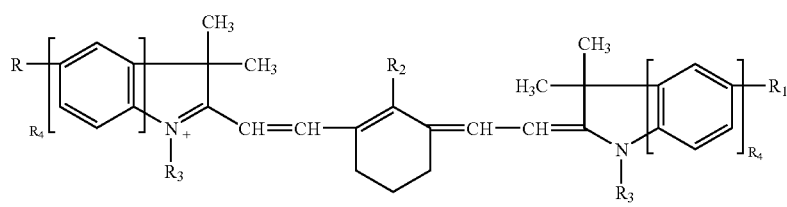

Figure 2:
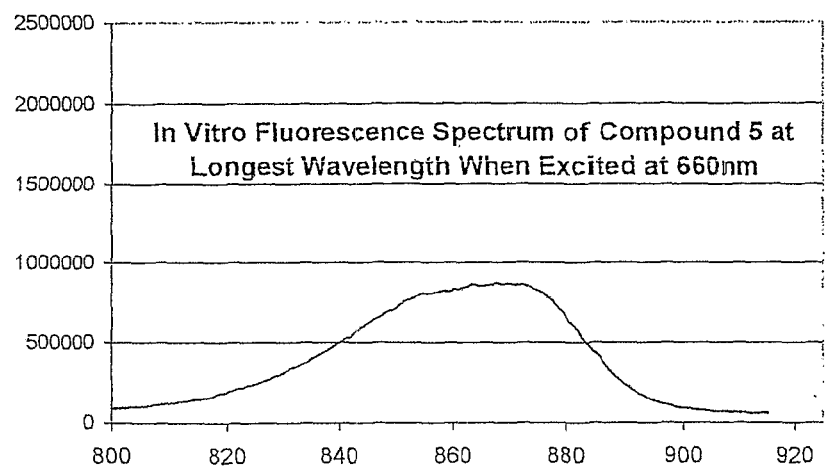
FIG. 2 is an in vitro fluorescence spectrum of conjugate 5 when excited of 660 nm.

R=COOH
R₁=CONH—(CH₂)n-Photosensitizer
R=R₁=CONH—(CH₂)n-Photosensitizer
Photosensitizer: Porphyrins, Chlorins, Bacteriochlorins, Phthalocyanines, Expanded Porphyrins.
R₂=halogens
R₃=Alkyl, Sulfonic acid or carboxylic groups containing carbon chains with variable carbon units.
R=CONH(CH₂)$_n$NH-folic acid As seen in FIG. 1, the UV-visible absorption spectrum of conjugate 5 exhibited characteristic absorption bands at 408, 660, and 830 nm corresponding to the 3-(1'-hexyloxyethyl) derivative of pyropheophorbide-a (HPPH) 4 and the modified long-wavelength absorbing dye 3 respectively and as best seen in FIG. 2 exhibited broad emission bands at 665, 710 and 860 nm indicating that the conjugate containing two chromophores (HPPH and the dye) is behaving like a single molecule.

Figure 3:
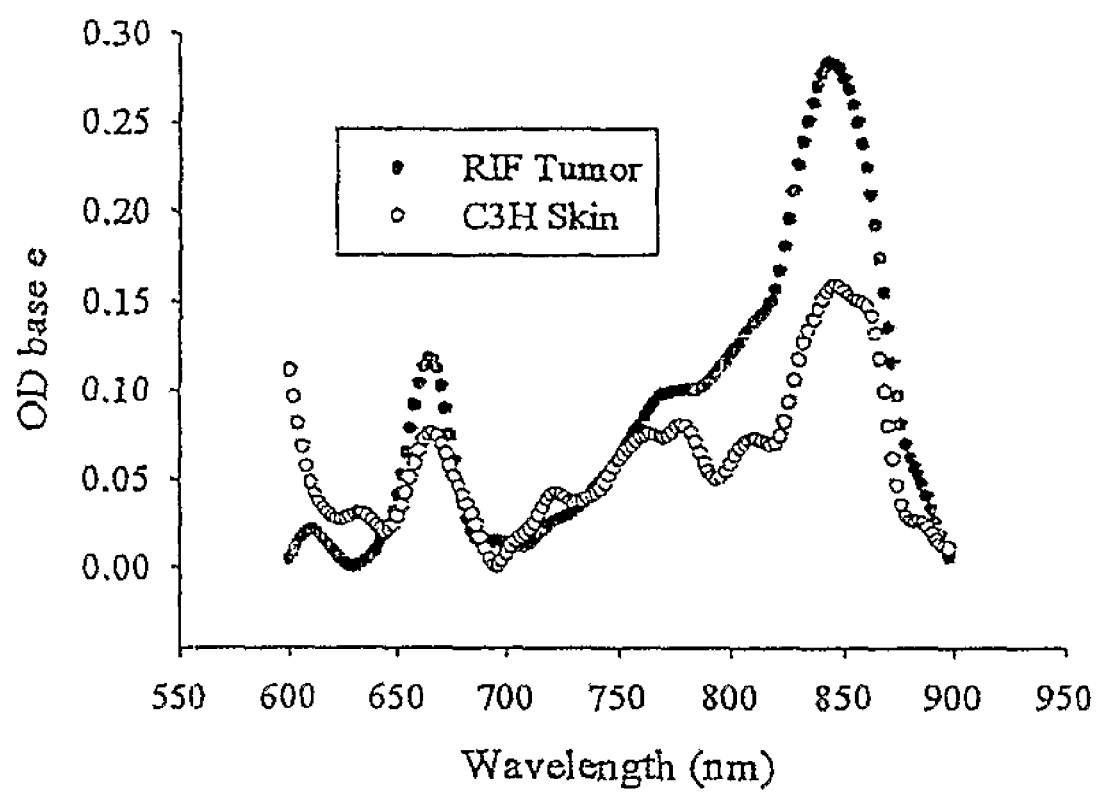
FIG. 3 is a graph showing relative uptake of conjugate 5 by tumor and skins at 24 hours post injection by relative fluorescence.
Figure 4:
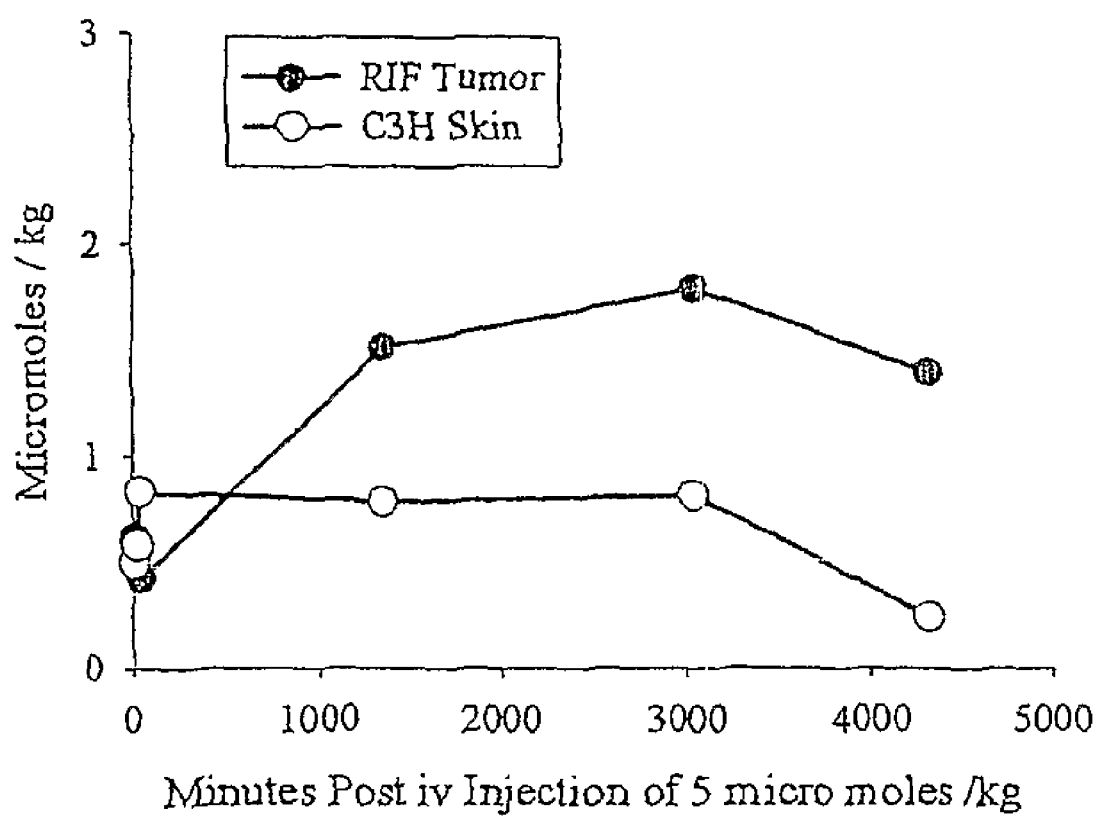
FIG. 4 shows a graph of relative uptake of conjugate 5 at 3-4 days post injection.

The tumor uptake of conjugate 5 was determined by in vivo reflectance spectroscopy. For these experiments, C3H mice bearing RIF tumors were injected with 5.0 µmole/kg of conjugate 5 and the in vivo absorption spectra were taken at various time intervals. As can be seen from FIG. 3, conjugate 5 shows a more significant uptake in tumor than skin at 24 hours post injection. At 3-4 days post injection (FIG. 4), the conjugates have cleared from the skin without significant decrease in tumor concentration. In contrast, the indocyanine green analog (1), referred to herein as ICG, alone at the same dose (5.0 µmole/kg) produced higher uptake in skin than in tumor (C3H mouse bearing tumor) and compared with HPPH-ICG conjugate 5, the ICG analog alone showed a significantly lower tumor uptake (FIG. 5). The ICG dye (1) was found to clear rapidly from both tumor and skin at 4-5 hours post injection. These results clearly suggest that in conjugate 5, HPPH not only served as a vehicle to deliver the dye with a required photophysical characteristic to tumor, but also served as a vehicle in retaining dye in tumor apparently by changing overall pharmacokinetic characteristic of the conjugated molecule as compared with the dye or photosensitizer alone.

In vivo fluorescent spectra of conjugate 5 were determined by in vivo fluorescent spectroscopy at variable concentrations (10, 5.0, and 2.5 µmole/kg). The results are summarized in FIG. 6. In a typical experiment, conjugate 5 was injected into each mouse (in a group of three mice bearing RIF tumors) at a dose of 10, 5.0 and 2.5 µmoles/kg. At 24 hours post injection, the absorption peak at 660 nm was excited and the longest wavelength emission (broad band from 830-890 nm) was recorded. At variable concentrations, the resulting fluorescence with equal intensity is possible due to a saturation effect.

To measure photosensitizing efficiency, RIF tumors were implanted subcutaneously into axilla of 5-7 week old female C3H mice. When tumors grew to about 4 to 5 mm³ in size, conjugate 5 was injected at variable doses (0.5, 1.0, 1.5, and 2.5 µmole/kg) The tumors were treated with light at an energy of 135 J/cm² at a wavelength of 665 nm (in vivo absorption band for HPPH) at 24 hours post injection and the mice were observed daily. From the results summarized in FIG. 7, it can be seen that conjugate 5 produced 100% tumor cure at a dose of 2.5 µmole/kg (the tumor imaging dose). At lower doses, limited photosensitizing efficacy was observed.

In general, porphyrin based compounds have shown diverse patterns of localization at least somewhat dependent upon structure, lipophilicity and charge. Localization in lysosomes and mitochondria have been reported to be dominant; however, the photosensitizers that predominately localize in mitochondria have generally been found to be more effective. Therefore, the site of localization of the HPPH-ICG conjugate 5 (2.5 µmole/kg) was compared with a known mitochondrial probe (MITO-TRACKER® green (400 nM) in RIF tumor cells (a well known tumor cell line) after 24 hours incubation. The results shown in FIG. 8 clearly indicate that conjugate 5 localizes in mitochondria, a more sensitive site for cell damage for photodynamic therapy (PDT). A in FIG. 8 shows the localization of compound 5 in mitochondria. B in FIG. 8 shows localization of the known mitochondrial probe and C shows an overlay of A and B.

The results show that the tumor avid porphyrin based photosensitizers can be used as vehicles for delivering dyes to tumors that are not otherwise tumor specific but exhibit strong emission in the IR region of the spectrum. In particular HPPH conjugated with an isocyanine derivative was specifically shown to localize in tumors permitting detection by fluorescence while still maintaining the property of being tumor destructive upon exposure to light. This result is predictive of the properties of other porphyrin based photosensitizers conjugated with other dyes having similar absorption and emission properties. The methodology thus provides the means for producing a variety of conjugates in which the photosensitizing moiety can be replaced with a series of long-wavelength tumor avid photosensitizers, e.g. purpurinimides and bacteriochlorins exhibiting long wavelength absorptions in the range of 700-800 nm. Compared to compound 5, these other conjugates provide the ability to excite the molecule at the longer wavelength absorption (700-800 nm, instead of 660 nm for HPPH) and detect emission at more than 860 nm. This is a unique advantage offered by the conjugates of the invention. In addition, the compounds of the invention have the advantage of treating larger tumors by implanting fewer fibers for delivering light at the appropriate wavelength.

The development of tumor avid optical imaging agents in accordance with the present invention would in itself be a marked advance but the dual function nature of the compounds of the invention for the first time presents the opportunity for diagnosis followed by targeted photodynamic therapy, combining two modalities into a single cost effective "see and treat" approach.

The following example illustrates a preferred method for synthesis of compounds of the invention.

Synthesis of ICG Analog 3:

The commercially available dye 1 (60 mg) and 4-aminothiophenol 2 (60 mg) were dissolved in dry DMF and stirred overnight. After removing the solvent, the residue was purified by silica column chromatography using MeOH/CH₂Cl₂ (1:3) as the eluting solvent, and the intermediate 3 was obtained in ~60% yield. UV-vis: 830 nm (in MeOH) (ε=207,000). ¹H NMR (CHCl₃), δ (ppm) 9.0 (d, 2H, H-a), 8.2 (d, 2H, H-b), 8.0 (t, 4H, H-c), 7.62 (d, 4H, H-d), 7.48 (2d overlapped to be triplet, 2H, H-e), 7.12 (d, 2H, H-f), 6.70 (d, 2H, H-g), 6.35 (d, 2H, H-h), 4.30 (t, 4H, H-i), 2.95 (t, 4H, H-j), 2.80 (m, 4H, H-k), 2.00 (m, 10H, 4H for H-1), 6H for m, n, o), 1.90 (s, 12H, H-p), 1.30 (s, H-q). MS analysis for 3 (C₅₂H₅₆N₃NaO₆S₃): 937, Found: 938

Synthesis of HPPH-ICG Conjugate 5:

The hexyl ether derivative of pyropheophorbide (HPPH) 4 (100 mg) and DCCI (110 mg) were dissolved in DMF (1 ml). After stirring for 10 minutes, the solution of 3 (60 mg) in DMF (2 ml) and DMAP (10 mg) were added. After stirring the reaction mixture for 24 h, it was diluted with dichloromethane (100 ml), washed with water (2×100 ml). The organic phase was dried over anhydrous sodium sulfate. The residue obtained after removing the solvent from the filtrate was purified by chromatography using MeOH/CH₂Cl₂ (1:3)

as the eluting solvent and the desired conjugate 5 was obtained in ~65% yield. UV-vis in $H_2O$: 848 nm ($\epsilon$=975,47), 664 nm ($\epsilon$=53,800), 413 nm ($\epsilon$=101'456). UV-vis in MeOH: 833 nm ($\epsilon$=207, 455), 660 nm ($\epsilon$=53,856), 408 nm ($\epsilon$=95, 222). $^1$H NMR ($CHCL_3$), δ (ppm): 9.47 (s, 1H, meso-H in HPPH part), 8.46 (s, 1H, meso-H in HPPH part), 8.35 (br-s, 3H, 1H for meso-H in HPPH part, 2H for H-a), 7.50 (m, 5H, 1H for H-b, 4H for H-c), 7.30 (m, 3H, 1H for H-b, 2H for H-e), 7.20 (s, 2H, H-f), 7.05 (s, 4H, H-d), 6.85 (s, 2H, H-g), 6.61 (s, 2H, H-h), 5.70 (br, 3H, 1H for H-$3^1$, 1H for H-17, 1H for H-18), 4.54 (br-doublet, 1H, H-$13^2$), 4.22 (br, 2H, H-i), 3.66 (br, 2H, H-i), 3.52 (br, 1H, H-$13^2$), 3.20 (br, 9H, 5H for HPPH part: 3H for 7-$CH_3$, 2H for $3^1$-$OCH_2(CH_2)_4CH_3$, 4H for H-j), 3.03 (m, 4H, H-k), 2.90 (s, 1H, $\overline{=CONH}$—), 2.72 (br, 7H, 2H for 8-$CH_2CH_3$, 2H for 17-$CH_2CH_2\overline{CO}$—, 3H for 2-$CH_3$), 2.55 (br, $\overline{5H}$, 2H for 17-$CH_2CH_2CO$—, 3H for 12-$\overline{CH}_3$), 1.88 (br, 3H, 3-$CHCH_3$), 1.72-$\overline{0.72}$ (many multiples, 36 protons, 22 H for dye part: 12H for H-p, 4H for H-1, 6H for H-m, n, o; 14 H for HPPH part: 3H for 18-$CH_3$, 3 H for 8-$CH_2CH_3$, 8H for $3^1$-$OCH_2(CH_2)_4CH_3$), $0.6\overline{2}$ (m, 3H, $3^1$-$O\overline{CH_2(}CH_2)_4CH_3$. MS for conjugate 5 ($C_{91}H_{102}N_7NaO_9\overline{S_3}$): 1555.7, Found: 1556.7.

What is claimed is:

1. A compound having preferential localization in tumor tissue relative to normal tissue, a preferential electromagnetic absorption at a wavelength between about 660 and 900 nm, and a fluorescence at a wavelength shifted from the preferential absorption by at least +30 nm, said compound being a conjugate of a tumor avid tetrapyrrole compound with a fluorescent dye said compound having the formula:

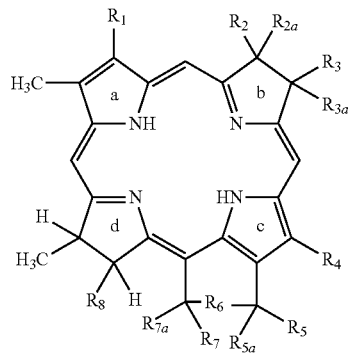

where:
$R_1$ is, substituted or unsubstituted, —CH=$CH_2$, —CHO, —COOH, or

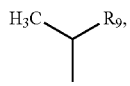

where $R_9$=—$OR_{10}$ where $R_{10}$ is lower alkyl of 1 through 8 carbon atoms, or —($CH_2$—O)$_n CH_3$;

$R_2$, $R_{2a}$, $R_3$, $R_{3a}$, $R_4$, $R_5$, $R_{5a}$, $R_7$, and $R_{7a}$ are independently hydrogen, lower alkyl, substituted lower alkyl, lower alkylene or substituted lower alkylene or two $R_2$, $R_{2a}$, $R_3$, $R_{3a}$, $R_5$, $R_{5a}$, $R_7$, and $R_{7a}$ groups on adjacent carbon atoms may be taken together to form a covalent bond or two $R_2$, $R_{2a}$, $R_3$, $R_{3a}$, $R_5$, $R_{5a}$, $R_7$, and $R_{7a}$ groups on the same carbon atom may form a double bond to a divalent pendant group; $R_2$ and $R_3$ may together form a 5 or 6 membered heterocyclic ring containing oxygen, nitrogen or sulfur; $R_6$ is —$CH_2$—, —$NR_{11}$—, where $R_{11}$ is, substituted or unsubstituted, lower alkyl, or lower alkylene; or a $R_6$ is a covalent bond; $R_8$ is —($CH_2)_2CO_2R_{12}$ where $R_{12}$ is, substituted or unsubstituted, lower alkyl, lower alkylene or —$NH_2$, wherein at least one of $R_1$, $R_{2a}$, $R_3$, $R_{3a}$, $R_4$, $R_5$, $R_{5a}$, $R_7$, $R_{7a}$, $R_8$, $R_9$, $R_{10}$, $R_{11}$, or $R_{12}$ is substituted with a dye fluorescing at a peak emission wave length of from about 800 to about 900 nm and having a peak absorption at least 30 nm below its peak emission.

2. The compound of claim 1 wherein the shift is at least +50 nm.

3. The compound of claim 1 wherein the fluorescent dye is an indocyanine dye.

4. The compound of claim 1 wherein the tumor avid tetrapyrrole compound is selected from the group consisting of chlorins, bacteriochlorins and porphyrins.

5. The compound of claim 4 wherein the dye is an indocyanine dye.

6. The compound of claim 4 wherein the dye is indocyanine green.

7. The compound of claim 1 having the structural formula:

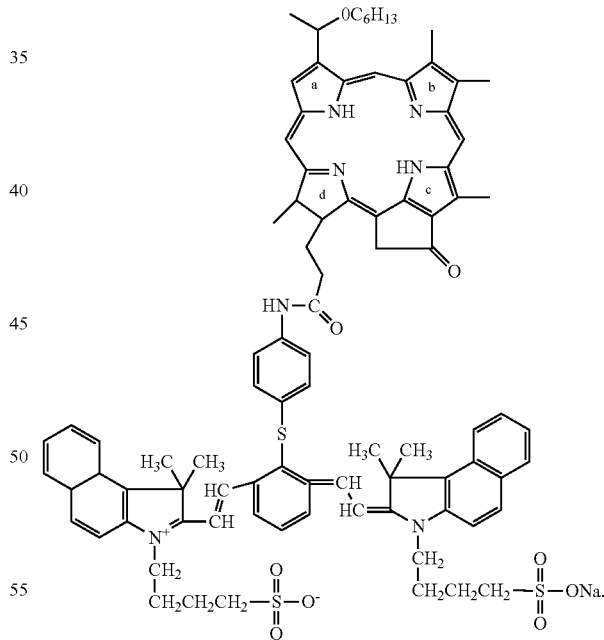

* * * * *